United States Patent
Wieland (10) Patent No.: US 8,038,679 B2
(45) Date of Patent: Oct. 18, 2011

(54) REAMING DEVICE

(75) Inventor: Manfred Wieland, Kiel (DE)

(73) Assignee: Stryker Trauma GmbH (DE)

( * ) Notice: Subject to any disclaimer, the term of this patent is extended or adjusted under 35 U.S.C. 154(b) by 1121 days.

(21) Appl. No.: 11/805,423

(22) Filed: May 23, 2007

(65) Prior Publication Data

US 2008/0294168 A1 Nov. 27, 2008

(51) Int. Cl.
*A61B 17/00* (2006.01)
(52) U.S. Cl. ......................................................... 606/80
(58) Field of Classification Search .............. 606/80–85; 175/273, 279, 280, 286–289
See application file for complete search history.

(56) References Cited

U.S. PATENT DOCUMENTS

| | | | | |
|---|---|---|---|---|
| 391,899 | A * | 10/1888 | Plom et al. ..................... | 175/202 |
| 963,596 | A * | 7/1910 | Lescure ........................ | 408/159 |
| 2,649,001 | A * | 8/1953 | Fennell ........................ | 408/158 |
| 2,816,552 | A * | 12/1957 | Hoffman ....................... | 606/159 |
| 3,702,611 | A * | 11/1972 | Fishbein ....................... | 606/81 |
| 4,131,116 | A * | 12/1978 | Hedrick ........................ | 606/81 |
| 4,498,468 | A | 2/1985 | Hansson | |
| 5,030,201 | A | 7/1991 | Palestrant | |
| 5,505,738 | A | 4/1996 | Hempel et al. | |
| 5,546,267 | A | 8/1996 | Frederiksen et al. | |
| 5,562,665 | A | 10/1996 | Young | |
| 5,591,170 | A | 1/1997 | Spievack et al. | |
| 5,810,820 | A | 9/1998 | Santori et al. | |
| 5,827,323 | A | 10/1998 | Klieman et al. | |
| 6,110,176 | A * | 8/2000 | Shapira .......................... | 606/80 |
| 6,174,313 | B1 * | 1/2001 | Bonutti .......................... | 606/80 |
| 6,283,971 | B1 * | 9/2001 | Temeles ......................... | 606/81 |
| 6,676,665 | B2 | 1/2004 | Foley et al. | |
| 6,746,451 | B2 | 6/2004 | Middleton et al. | |
| 6,863,672 | B2 | 3/2005 | Reiley et al. | |
| 7,179,024 | B2 * | 2/2007 | Greenhalgh .................. | 408/224 |
| 2001/0034526 | A1 | 10/2001 | Kuslich et al. | |
| 2002/0018758 | A1 | 2/2002 | Hansenne et al. | |
| 2002/0183758 | A1 | 12/2002 | Middleton et al. | |
| 2003/0083681 | A1 | 5/2003 | Moutafis et al. | |
| 2003/0130664 | A1 | 7/2003 | Boucher et al. | |
| 2003/0233096 | A1 | 12/2003 | Osorio et al. | |
| 2004/0106940 | A1 * | 6/2004 | Shaolian et al. ............. | 606/170 |
| 2004/0267269 | A1 | 12/2004 | Middleton et al. | |
| 2005/0113836 | A1 | 5/2005 | Lozier et al. | |
| 2006/0064098 | A1 | 3/2006 | Hansson | |
| 2006/0241629 | A1 | 10/2006 | Krebs et al. | |
| 2007/0043373 | A1 | 2/2007 | Sala et al. | |

FOREIGN PATENT DOCUMENTS

| | | |
|---|---|---|
| DE | 10220253 | 11/2002 |
| GB | 2390028 | 12/2003 |
| JP | 2004604 | 1/1990 |
| JP | 2005152650 | 6/2005 |
| WO | 0047123 | 8/2000 |
| WO | 2007047065 | 4/2007 |

* cited by examiner

*Primary Examiner* — Nicholas Woodall
(74) *Attorney, Agent, or Firm* — Lerner, David, Littenberg, Krumholz & Mentlik, LLP (57) ABSTRACT

A bone reamer has an ablation device for forming cavities in body tissue, the ablation device is movable with respect to a head of the reamer, and is capable of protruding at least partially beyond a surface of the head. The amount of protrusion the ablation device protrudes beyond the surface of the head has a variable geometry and the geometry is remotely modifiable. More particularly, the amount the ablation device extends beyond the outer surface of a reamer head body can be varied by an actuator located on the reamer outside the body.

13 Claims, 6 Drawing Sheets

REAMING DEVICE

BACKGROUND OF THE INVENTION

The present invention relates to a bone reaming device, and in particular to a bone reaming device having an ablation device with a variable geometry, which geometry is remotely modifiable.

Surgeons are using minimally invasive surgical techniques on an increasing basis for the treatment of a wide variety of medical conditions. Such techniques typically involve the insertion of a surgical device through a natural body orifice or through a relatively small incision using a tube or cannula. In contrast, conventional surgical techniques typically involve a significantly larger incision and are therefore sometimes referred to as open surgery. Thus, as compared with conventional techniques, minimally invasive surgical techniques offer the advantages of minimizing trauma to healthy tissue, minimizing blood loss, reducing the risk of complications such as infection, and reducing recovery time. Further, certain minimally invasive surgical techniques can be performed under local anaesthesia or even, in some cases, without anaesthesia, and therefore enables surgeons to treat patients who would not tolerate the general anaesthesia required by conventional techniques.

Surgical procedures often require the formation of a cavity within either soft or hard tissue, including bone. Tissue cavities are formed for a wide variety of reasons, such as for the removal of diseased tissue, for harvesting tissue in connection with a biopsy or autogenous transplant, and for implant fixation. To achieve the benefits associated with minimally invasive techniques, tissue cavities should be formed by creating only a relatively small access opening in the target tissue. An instrument or device then can be inserted through the opening and used to form a hollow cavity that is significantly larger than the access opening. Depending on the specific application, the shape of the desired cavity can be spherical, hemispherical or cylindrical, or any number of different combinations or variations of such shapes.

A tissue cavitation device and method is, for example, known from US 2002/0183758 A1, describing a percutaneous surgical device and method for creating a cavity within tissue during a minimally invasive procedure. The cavitation device includes a shaft interconnected to a flexible cutting element. The flexible cutting element has a means to move toward a shape suitable for forming a cavity in tissue.

Further, a surgical rotary abrader is known from US 2003/0083681 A1, describing an apparatus for use as a surgical hand piece including a body, a rotatable shaft extending from the body and including a tissue contacting component such as a burr, and an outer tube connected to the body and surrounding at least a portion of the shaft.

However, presently known solutions for a reaming device lack of a capability of tracking particular forms of the cavity to be formed owing to the more or less fixed geometry of the head of such devices.

SUMMARY OF THE INVENTION

It may be seen as one aspect of the present invention to provide a reaming device being capable of tracking a particular form of a cavity to be formed, for example, to minimise the dimension of the cavity and to avoid collisions with obstacles, for example, implants.

According to an exemplary embodiment of the invention, there is provided a reaming device comprising a first shaft, a head having a surface, which head is pivoted or rotatable with respect to the first shaft, an ablation device, the ablation device being axially movable with respect to the head and being capable of protruding at least partially beyond the surface of the head, wherein a protruding amount the ablation device protrudes beyond the surface of the head has the variable geometry and the geometry is remotely modifiable.

Thus, it is possible to modify the geometry of the head of the reaming device during operation without the need to remove the total reaming device from the operation location. Owing the known structure and total geometry, the protruding geometry may be set without the need to monitor the present protruding geometry. If, for example, monitored by an imaging system like x-ray or computer tomography and the like, it is possible to modify the geometry of the ablation device in order to more exactly track a particular form of the cavity to be formed by the reaming device. It is further possible to avoid, for example, a collision of the rotating ablation device with an obstacle. An obstacle may be, for example, an implant, in particular an intramedullary nail. In particular, by modifying the geometry of the ablation device, it is possible to modify the diameter of the cavity without the need to modify, for example, the rotational speed of a head of a reaming device.

According to an exemplary embodiment of the invention, the ablation device protrudes at least partially beyond the surface of the head with at least a lateral component.

Thus, in particular, the radius of the cavity to be formed may be modified, so that it is possible to track a particular form of a tubular cavity. The rotational axis in this case may be substantially the longitudinal axis of the reaming device.

According to an exemplary embodiment of the invention, the reaming device further comprises a second shaft, the second shaft being coupled to the head, wherein the second shaft being pivoted with respect to the first shaft and being capable of pivoted driving the head with respect to the first shaft.

Thus, it is possible to remotely modify the geometry of the protruding amount of the ablation device protruding beyond the surface of the head. Further, it is possible to drive the head by a drive being located outside the head portion of the reaming device. In particular, the second shaft may be used for driving the head and the ablation device. However, instead of driving the head by the second shaft, it is possible to drive the head, for example, by a driving unit being located in the head of the reaming device. Such a drive may be, for example, a turbine placed close to the head, which may be driven by pressured air, so that the pressured air is let through the first shaft to drive the turbine. The pressured air after leaving the turbine may also be used for removing ablated tissue.

According to an exemplary embodiment of the invention, the second shaft is substantially concentric within the first shaft.

Thus, the outer surface of the shaft of the reaming device may be kept in a more or less constant position. In other words, when placing the second shaft within the first shaft, the first shaft may be kept fixed, wherein the second shaft may rotate to drive the head of the reaming device. Thus, vibrations and damages to the tissue surrounding the first shaft as an entry channel of the target tissue may be avoided.

According to an exemplary embodiment of the invention, the reaming device further comprises a third shaft, the third shaft being coupled to the ablation device, wherein the third shaft being capable of modifying the variable geometry of the protruding amount of the ablation device protruding beyond the surface of the head.

Thus, it is possible to remotely modify the geometry of the protruding amount of the ablation device by a shaft, so that the reaming device dimensions, in particular the diameter of the outer shell, may be kept low.

According to an exemplary embodiment of the invention, the third shaft is substantially concentric within the second shaft.

Thus, the second shaft may rotate, wherein the third shaft may be kept fixed in order to modify the geometry of the protruding amount. However, it is also possible to rotate the third shaft. By providing a second shaft and a third shaft, it is possible to divide the functions of driving the head with the ablation device and the modification of the geometry by having two different mechanical components. However, the driving of the head and the modification of the driving geometry each may be carried out by means of a micro turbine, as described above or an electric micro-drive, so that the second shaft and the third shaft, respectively, may be replaced by e.g. an electrical connection. Further, the second shaft may be omitted, in case the third shaft is used for both purposes at the same time, driving the head and for modifying the variable geometry. In this case, the connection between the head and the first shaft should be pivoted and non-positive and force-fit, respectively, in the axial direction.

According to an exemplary embodiment of the invention, the reaming device comprises at least one ablation wire protruding at least partially beyond the surface of the head through a through-hole within the head, wherein the third shaft being coupled with the ablation device and being axially movable with respect to the head.

Thus, it is possible to move the tip of an ablation wire to modify the geometry of the protruding amount. The protruding amount corresponds to the portion of the tip of the ablation wire, which extends beyond the surface of the head. When providing a flexible ablation wire, the geometry of the protruding amount and the radius of the operating area of the reaming device may be modified in order to track a particular diameter of a, for example, tubular cavity of varying diameter over the length formed by the reaming device. The tip of the ablation wire may be provided with a burr or an ablation tool in order to remove tissue.

According to an exemplary embodiment of the invention, the ablation device comprises at least one ablation element protruding at least partially beyond the surface of the head through a through-hole within the head, wherein the third shaft being coupled with the ablation device via a gear to modify the variable geometry of the protruding amount protruding beyond the surface of the head.

Thus, the ablation elements may be formed of a non-flexible material in order to provide a hard or rigid ablation element. Such rigid ablation elements are, for example, necessary if removing of hard tissue is desired, for example, within bones.

According to an exemplary embodiment of the invention, the head comprises at least one recess, and the reaming device further comprises a conduit which conduit is connected via a first end to the recess to allow removal of ablated tissue.

Thus, it is possible to remove tissue from the operating area of the reaming device head so that ablated tissue does not remain in the cavity. Further, it is possible to deliver particular materials through the conduit to the head of the reaming device, for example, pharmaceuticals for treating the area of the cavity formed by the reaming device.

According to an exemplary embodiment of the invention, the conduit is formed by an inner wall of the first shaft and an outer wall of one out of the group consisting of the second shaft and the third shaft. Thus, the conduit may be formed as a concentric space between the shafts, so that no further conduit outside the first shaft needs to be provided.

According to an exemplary embodiment of the invention, the head is pivoted around a longitudinal axis of the first shaft. Thus, the head may be formed very slim in order to introduce the head of the reaming device through a bore hole or channel to the location to be treated with the reaming device.

According to an exemplary embodiment of the invention, the head is mounted on a first end of the first shaft, and a second end of the first shaft is mounted to a suction adapter. Thus, the removed ablated tissue may be sucked via the suction adapter, which suction adapter may be connected to a vacuum pump or the like.

It should be noted that the above features may also be combined. The combination of the above features may also lead to synergetic effects, even if not explicitly described in detail.

These and other aspects of the present invention will become apparent from and elucidated with reference to the embodiments described hereinafter.

BRIEF DESCRIPTION OF THE DRAWINGS

Exemplary embodiments of the present invention will be described in the following with reference to the following drawings.

DETAILED DESCRIPTION

Figure 1:
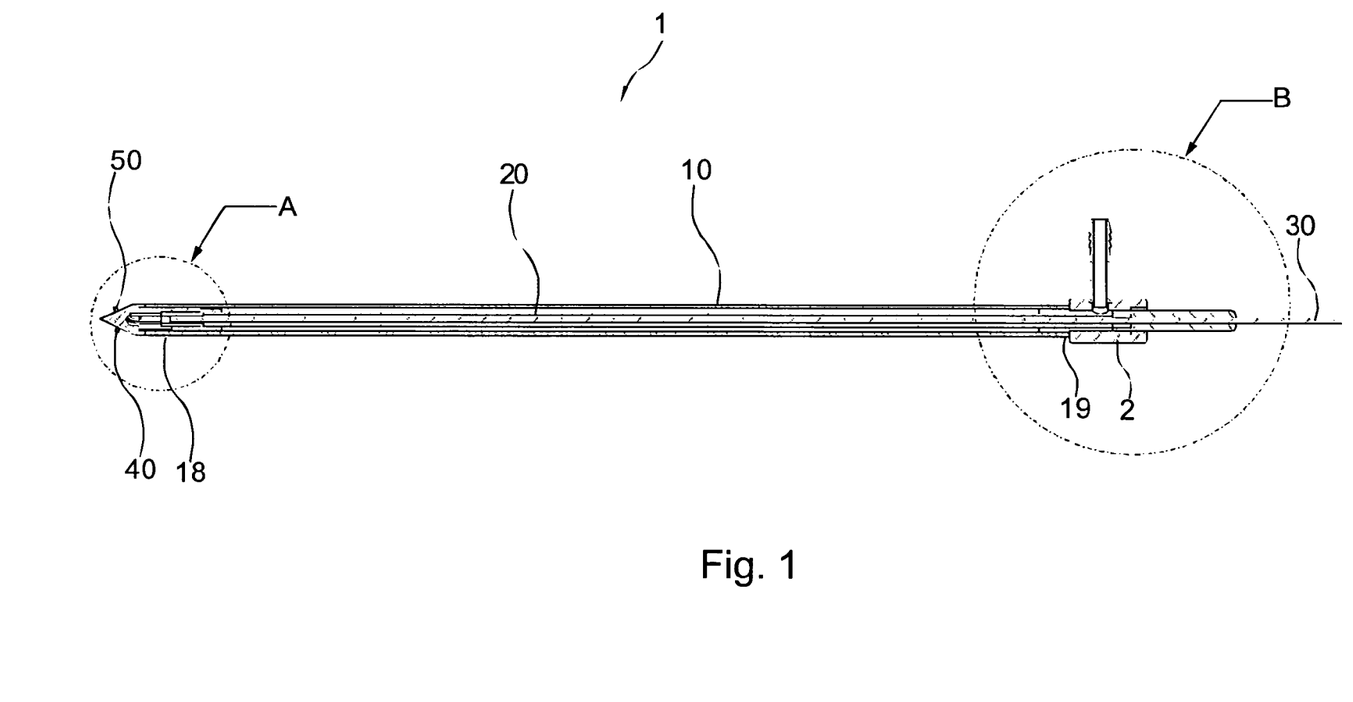
FIG. 1 illustrates a longitudinal cross-section of a reaming device according to an embodiment of the present invention.

FIG. 1 illustrates a total view of the reaming device according to an exemplary embodiment of the invention. The reaming device has a head portion denoted with A, an operator portion denoted with B and a shaft portion between the head portion and the operator portion. The head portion will be inserted through an orifice or channel of the human body in order to remove or ablate tissue by means of ablation devices 50. The operator portion denoted with B remains outside the human body in order to allow the operator to handle the reaming device. For example, it is possible to remove the ablated tissue by sucking on a suction adapter or a suction device 2, when an operator handles the reaming device, in particular the shaft 30 for modifying the geometry of the protruding amount of an ablation device, which protrudes beyond an outer surface of a head portion 40. The head 40 portion is mounted on to a first shaft 10, in particular, the head is pivoted with respect to the first shaft 10. In the shown embodiment, a second shaft 20 is provided concentrically within the first shaft in order to drive the head 40. The head 40 is mounted to one end 18 of the first shaft 10, and with a second end 19 of the first shaft 10, the first shaft is mounted to the suction adapter 2. Thus, a reaming device 1 may be provided, which allows an operator to modify the geometry of a protruding amount of an ablation device by means, for example, of a third shaft 30.

Figure 2:
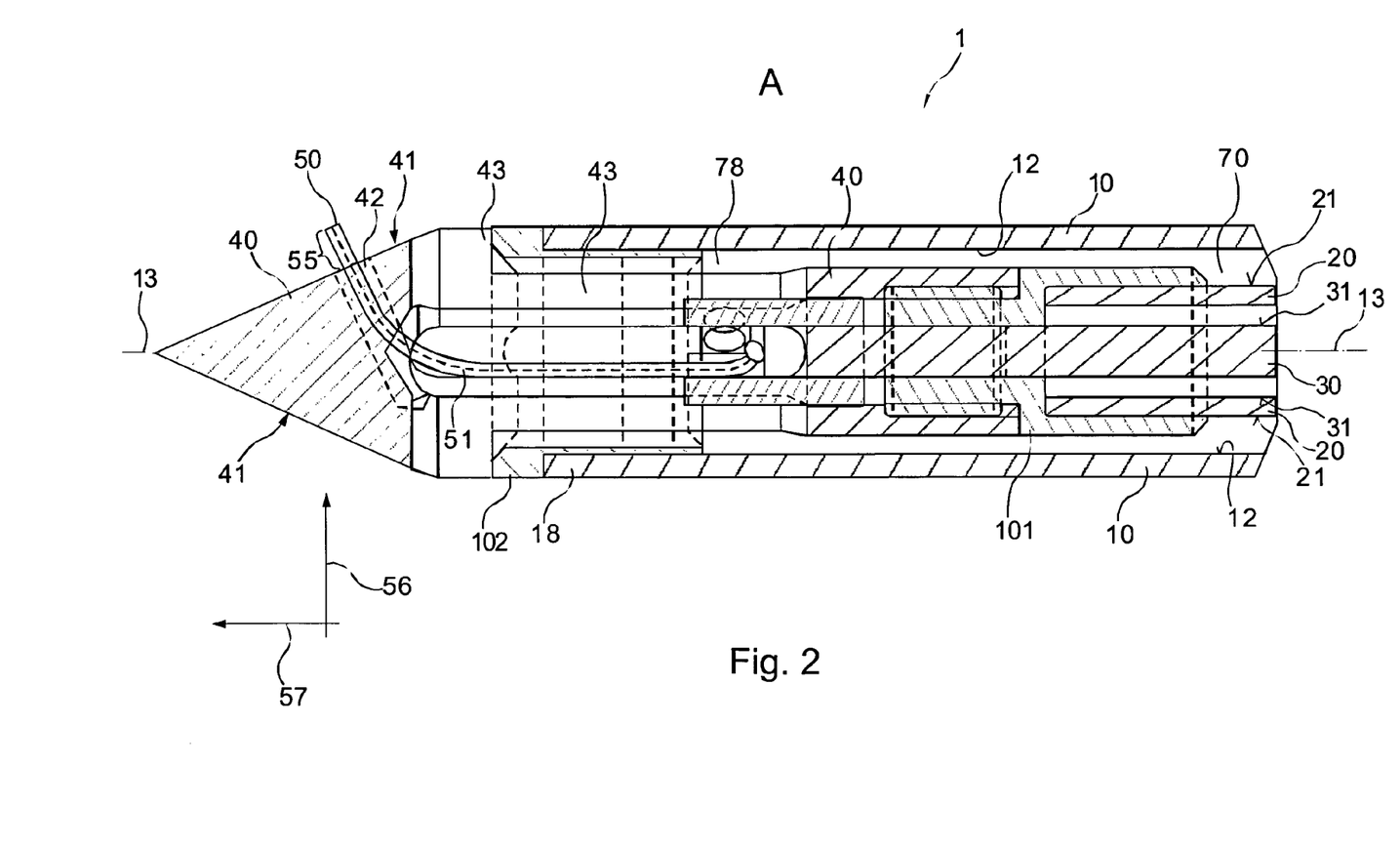
FIG. 2 illustrates a longitudinal cross-section of a head portion of a reaming device according to an embodiment of the present invention.

FIG. 2 illustrates a detailed picture of a longitudinal cross-section of the head 40 of the reaming device 1. The head portion denoted with A comprises a first shaft 10, a second shaft 20 being concentrically formed within the first shaft and a third shaft 30 provided concentrically within the second shaft 20 in the present embodiment. The head 40 may be mounted to the top portion 18 of the first shaft 10 by means of an adapter plug 102, which may also serve as a gasket or seal. The ablation device 50 may comprise, for example, an ablation wire 51, which protrudes with a protrusion a mount 55 beyond a surface 41 of the head 40. The protrusion wire may extend through a hole or opening 42 being formed in the head 40 of the reaming device 1. The head 40 may be pivoted or rotated around a longitudinal axis 13 of the shaft geometry, so that also the protruding amount 55 rotates in order to ablate tissue. The protruding amount 55 extends at least partially laterally in radial direction 56 with respect to the longitudinal axis 13 of the device. However, the protruding amount 55 may also extend partially in a longitudinal direction 57, i.e. into the direction of the longitudinal axis 13.

Further, openings 42, 43 may be provided in order to allow removal of ablated tissue. These openings 43, 42 may be provided close to the ablation device 50 in order to allow removal of tissue immediately after ablating the tissue. The tissue may be removed by transporting the ablated tissue through the conduit 70, wherein the conduit 70 is functionally connected with its first end 78 to the openings or recesses 42, 43 to allow removal of the ablated tissue. The conduit may be formed by an inner wall 12 of the first shaft 10 and an outer wall 21 of second shaft 20 or may be formed by an inner wall 12 of the first shaft and an outer wall 31 of the third shaft 30. The latter case is applicable in case there is no second shaft provided. The coupling of the second shaft to the head 40 may be provided via an adapter device 101.

Figure 3:
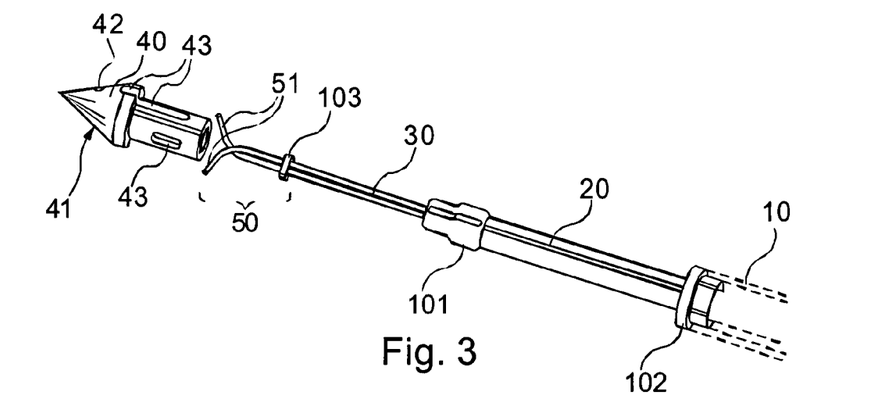
FIG. 3 illustrates an exploded view of several components of the reaming device according to an embodiment of the invention.

FIG. 3 illustrates an exploded view of the reaming device 1. The first shaft 10 is provided with the bearing, sealing and/or grommet device 102. The second shaft 20 is connected to the adapter device 101 in order to provide a connection to the head 40. Within the second shaft 20, there is provided the third shaft 30 on top of which, a block 103 may be provided in order to provide a reliable positioning of the ablation device 50. In the embodiment shown in FIG. 3, the ablation device comprises two ablation wires 51. The ablation wires, or in general, the ablation device 50, will be inserted into the head 40, so that the ablation wires 51 extend through the recesses or holes 42. The recesses 42 and 43 will serve for removal of the ablated tissue. A detailed geometry can be seen from the longitudinal cross-section of FIG. 2 or the perspective view of FIG. 4. It should be noted, that the number of ablation devices, e.g. ablation wires is not limited to the number of two, but may also be only one or alternatively more than two ablation devices.

Figure 4:
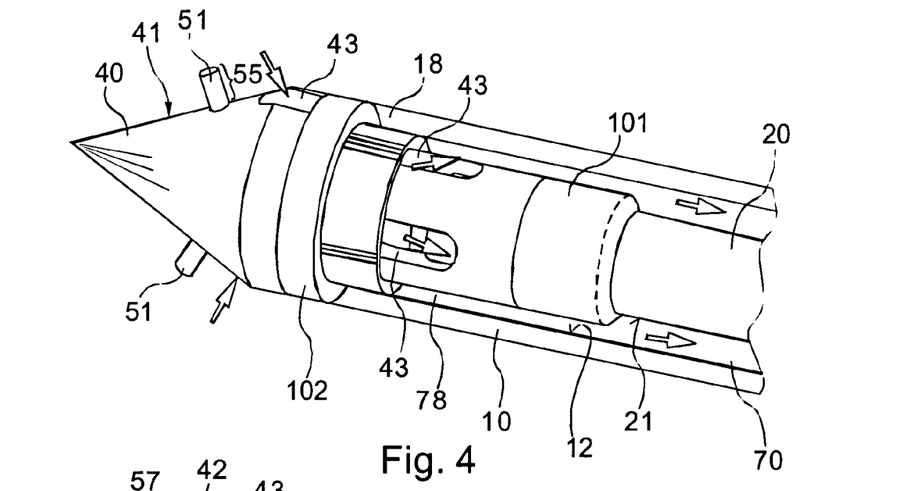
FIG. 4 illustrates a view of assembled components of a reaming device according to an embodiment of the invention.

FIG. 4 illustrates a perspective view of the assembled head portion of the reaming device 1. In the embodiment shown in FIG. 1, the first shaft 10 is connected to the head 40 via the device 102 serving as a sealing, bearing, and/or grommet. The adapter device 101 connects the second shaft being provided concentrically within the first shaft 10, to the head 40. The ablation wires 51 extend beyond the surface 41 of the head 40 by a protruding amount 55.

The geometry of the protruding amount may be remotely modified by moving the third shaft 30 for example in longitudinal direction, so that when pushing the third shaft 30, the protruding amount 55 of the protruding wires 51 will extend in a larger amount over the surface 41 of the head 40. It should be noted that the modification may also be carried out by a relative rotating and a gear, e.g. a screw or worm gear (not shown).

Recesses 43 allow removal of the ablated tissue. Therefore, the recesses 43 may be provided close to the protruding amount of the protruding wires 51. The arrows illustrate the flow of the ablated tissue from the proximity of the ablation wire 51 through the head portion through the recesses or openings 43 into the conduit 70. The conduit 70 is formed by the inner surface 12 of the first shaft 10 and the outer surface 21 of the second shaft 20. It should be noted that also the holes 42 through which the ablation device is conducted may serve as a recess to remove tissue.

It should be noted that the geometry of the ablation wires 51 may also be of a different geometry, in particular if modifying the tip geometry with respect to the requirements of the ablation application.

Figure 5:
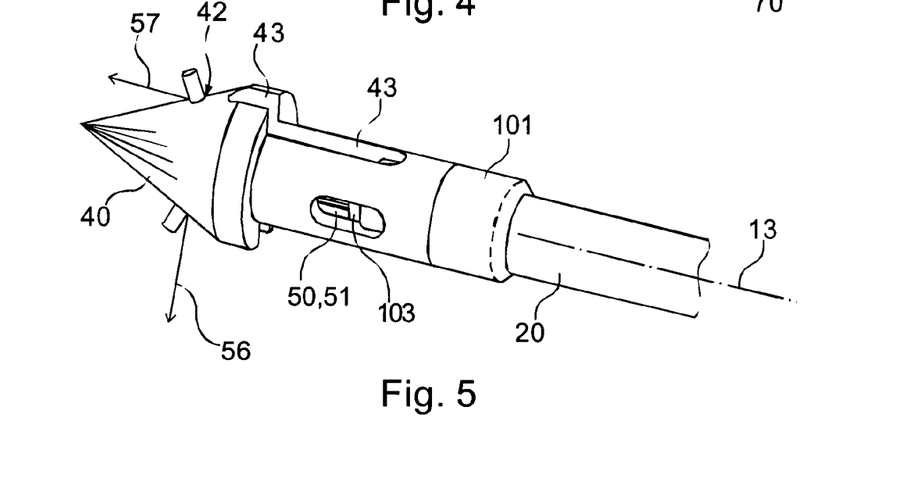
FIG. 5 illustrates an assembled head portion of a reaming device according to an embodiment of the invention.

FIG. 5 illustrates the head 40 with the ablation device 50 inserted into the holes 42 of the head 40, here in form of ablation wires 51.

The ablation wires 51 extend at least partially in a lateral direction 56 beyond the surface of the head 40, however they may also extend in a longitudinal direction 57. The block 103 restricts the movement of the ablation device and constitutes the transit from the ablation wires 51 to the third shaft 30.

Figure 6:
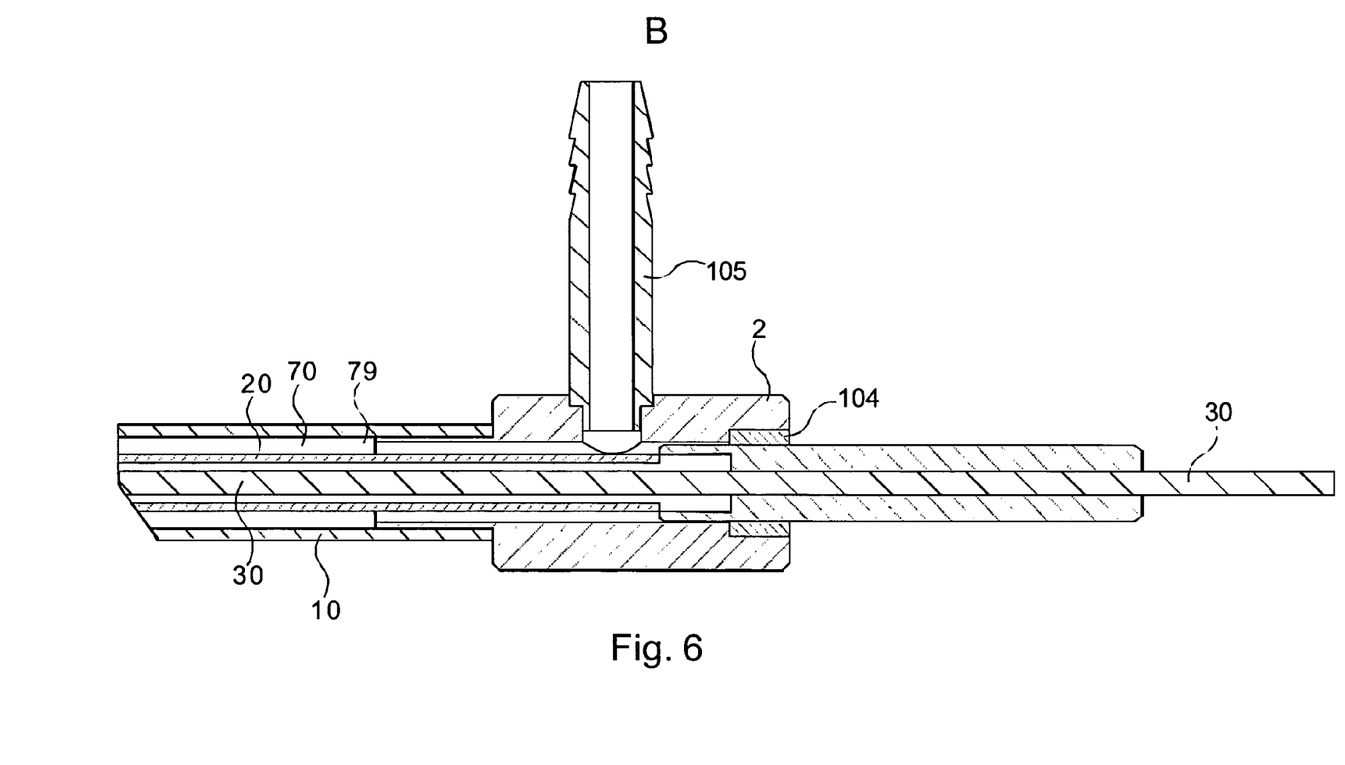
FIG. 6 illustrates the connection of the several shafts with the suction device according to an embodiment of the invention.

FIG. 6 illustrates a suction adapter 2, which may be connected to the end portion 79 of the conduit 70. The suction adapter 2 comprises, for example, a spout 105 to be connected to a vacuum pump, not shown. The second shaft may be connected to a drive, wherein the bushing may be sealed with a seal or grommet 104. The third shaft 30 may be formed concentrically within the second shaft. The handling devices or the driving devices for the second shaft 20 and the third shaft 30 are not shown.

Figure 7:
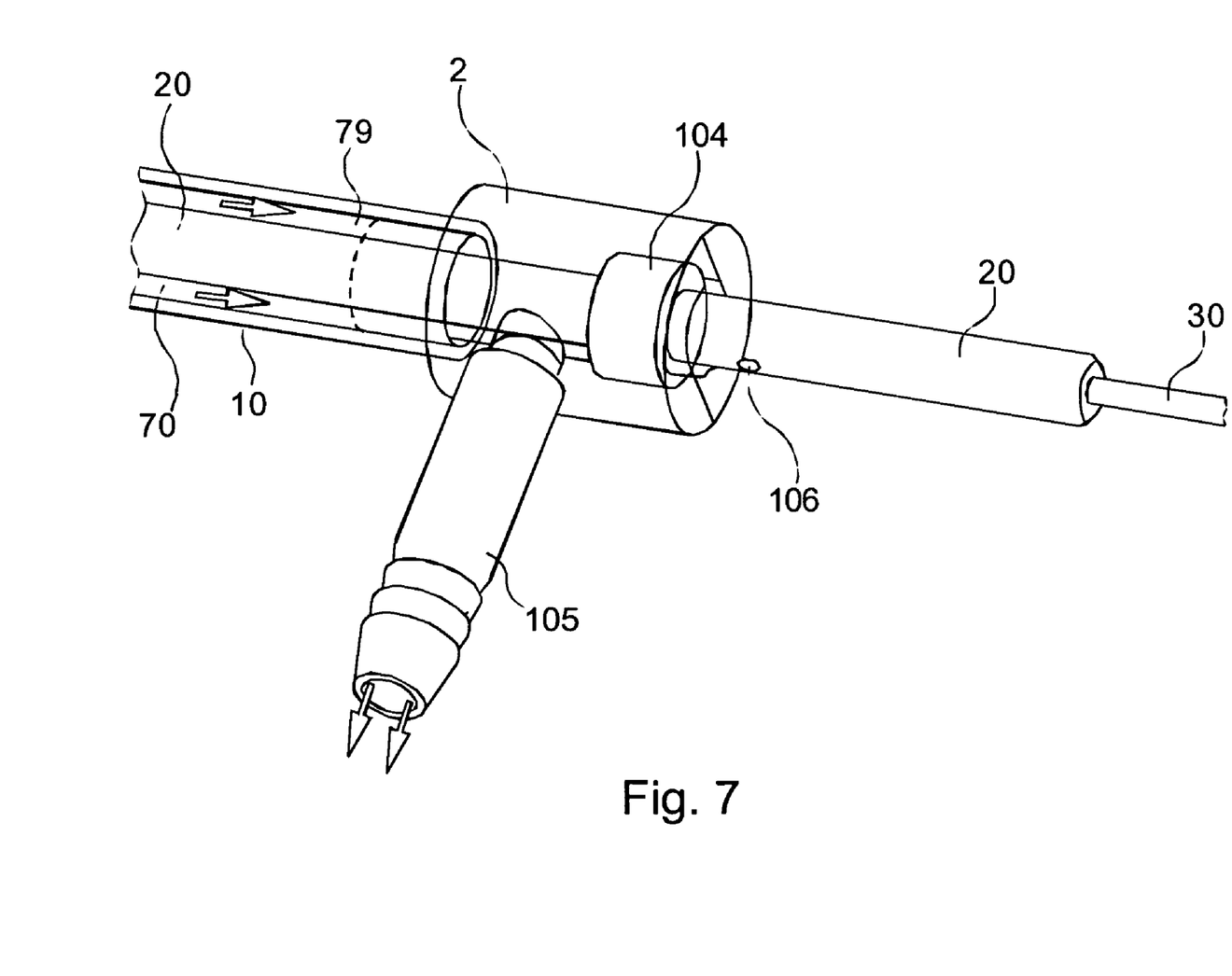
FIG. 7 illustrates a perspective view of the suction device according to an embodiment of the invention.

FIG. 7 illustrates a perspective view of the suction adapter 2 of FIG. 6. The end portion 79 of the conduit 70 is connected to the body of the suction adapter or suction device 2, so that the ablated tissue may be removed by a suction process. The ablated tissue will move along the arrows through the spout 105. The position of the second shaft 20 and a third shaft 30 may be fixed by a screw 106.

Figure 8:
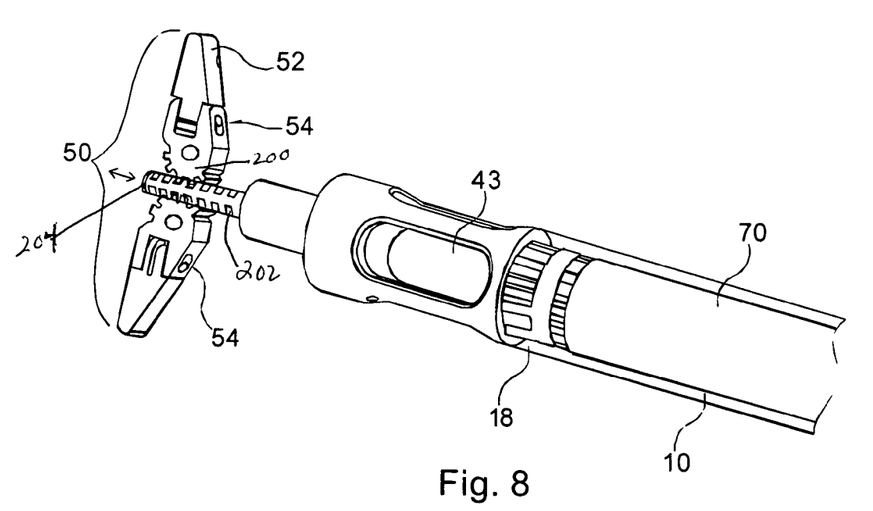
FIG. 8 illustrates a further embodiment including a gear arrangement within a head according to an embodiment of the invention.

FIG. 8 illustrates an embodiment including a gear providing a connection between the ablation device and the third shaft, not shown in FIG. 8. The ablation device shown in FIG. 8 comprises rigid or hard ablation tips or blades 52, which are pivoted mounted by a hinge 54 so that the rotation of the ablation device 50 is not locked when hitting a rigid obstacle, for example, an implant or the like. The gear wheel portions 200 engage into recesses 202 of a rod 204 which may be moved in the longitudinal direction, and which may be directly connected to the third shaft for modifying the geometry (diameter) of the ablation device. It should be noted that the gear wheel portions rotate along an axis perpendicular to the longitudinal axis of the device when being operated by the third shaft, which third shaft being moved into longitudinal direction of the device, i.e. the shaft extension. The tips or blades 52 of the ablation device 50 may rotate around a hinge 54, having a rotational axis being substantially parallel to the longitudinal axis of the device, if the device is in the position shown in FIG. 8. However, the rotational axis of the hinges 54 may be inclined, when the geometry of the ablating device 50 will be modified by moving the rod with the recesses along a longitudinal axis of the device. Similar to the previous embodiments, there may be provided recesses or openings 43 in order to remove tissue to be transported through the conduit 70.

Figure 9:
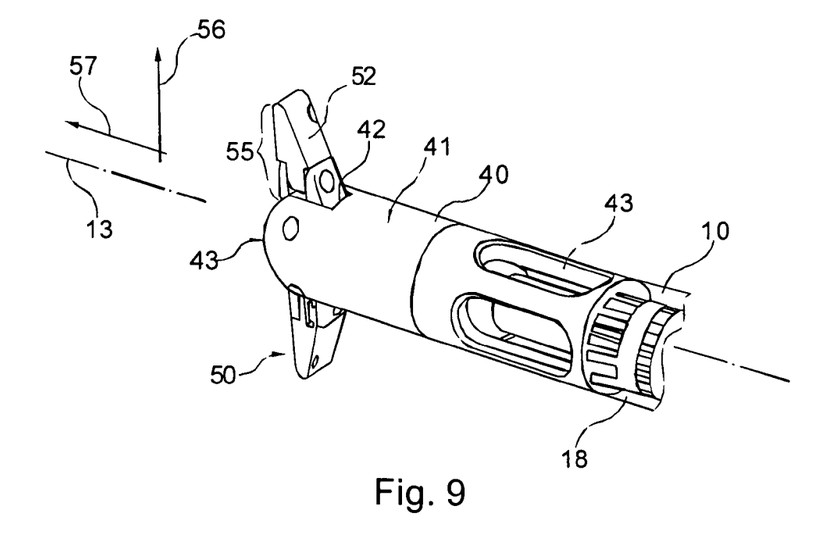
FIG. 9 illustrates an assembled arrangement of the embodiment illustrated in FIG. 8.

FIG. 9 illustrates the device of FIG. 8 when being assembled with a head 40, so that the mechanical parts are covered to avoid injury of the surrounding tissue or to avoid damages of the mechanical components.

It should be noted that the term 'comprising' does not exclude other elements or steps and the 'a' or 'an' does not exclude a plurality. Also elements described in association with different embodiments may be combined.

It should be noted that the reference signs in the claims shall not be construed as limiting the scope of the claims.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A bone reaming device comprising:
a first shaft extending along an axis;
a head having an outer surface, which head is rotatably mounted on the first shaft;
an ablation device, the ablation device being movable with respect to the head and being capable of protruding at least partially beyond the surface of the head, and
a third shaft, the third shaft being axially movable and coupled to the ablation device via a gear, wherein the gear includes a gear wheel portion rotatable about an axis perpendicular to the longitudinal axis of the device, the gear capable of being actuated to modify a variable geometry of a protruding amount of the ablation device,
wherein the protruding amount of the ablation device is variable by using a remote actuation device so that the variable geometry of the protruding amount is remotely modifiable,
wherein the ablation device comprises at least one ablation element protruding at least partially beyond the surface of the head through a through hole within the head,
wherein the ablation element comprises a hinge having a rotational axis being perpendicular to the axis of the gear wheel portion.

2. The reaming device as set forth in claim 1, wherein the ablation device when protruding at least partially beyond the outer surface of the head extends at least partially laterally of a longitudinal axis of the head.

3. The reaming device as set forth in claim 1, further comprising a second shaft, the second shaft being coupled to the head, wherein the second shaft being rotatable with respect to the first shaft and being capable of rotatably driving the head with respect to the first shaft.

4. The reaming device as set forth in claim 3, wherein the second shaft is substantially concentric and coaxial within the first shaft.

5. The reaming device as set forth in claim 1, wherein the third shaft is substantially concentric within the second shaft.

6. The reaming device as set forth in claim 1, wherein the outer surface of the head comprises at least one recess, and the reaming device further comprises a conduit, which conduit is connected at a first end to the recess to allow removal of ablated tissue.

7. The reaming device as set forth in claim 6, wherein the conduit is formed by an inner wall of the first shaft and an outer wall of one out of the group consisting of a second shaft coupled to the head and a third shaft coupled to the ablation device.

8. The reaming device as set forth in claim 7, wherein the head is rotated around a longitudinal axis of the first shaft by the second shaft, the second shaft mounted within the first shaft.

9. The reaming device as set forth in claim 7, wherein the head is rotatably mounted on a first end of the first shaft and a second end of the first shaft is mounted to a suction adapter.

10. A reamer for forming a cavity in body tissue comprising:
a first rotatable shaft extending along a longitudinal axis;
a cutting head mounted at a first end of the shaft, the head having at least one opening therein extending laterally of the longitudinal shaft axis; and
a cutting element mounted within the first rotatable shaft and having a first end extending through the opening in the head and a second end coupled to an actuator mounted adjacent a second end of the first rotatable shaft, and
a third shaft, the third shaft being axially movable and coupled to the cutting element via a gear, wherein the gear includes a gear wheel portion rotatable about an axis perpendicular to the longitudinal axis of the reamer, the gear capable of being actuated to modify a variable geometry of at least a portion of the first end of the cutting element extending through the opening,
wherein the actuator is capable of moving the first end of the cutting element within the opening of the head and laterally of an outer head surface while the first rotatable shaft is rotating, and
wherein the cutting element comprises a hinge having a rotational axis perpendicular to the axis of the gear wheel portion.

11. The reamer as set forth in claim 10 wherein the first rotatable shaft is surrounded by a stationary second shaft on which the cutting head is rotationally mounted.

12. The reamer as set forth in claim 11 wherein the head has a recess in communication with an interior portion of the second shaft.

13. The reamer as set forth in claim 12 wherein a suction device is connected to the second shaft and is in communication with the recess in the cutting head which communicates with the interior of the second shaft.

* * * * *